United States Patent
Lin et al.

(10) Patent No.: US 6,455,301 B1
(45) Date of Patent: Sep. 24, 2002

(54) ERYTHRITOL—PRODUCING MONILIELLA STRAINS

(75) Inventors: Shie-Jea Lin; Chiou-Yen Wen, both of Hsinchu; Chang-Cheng Huang, Keelung; Wen-Shen Chu, Hsinchu, all of (TW)

(73) Assignee: Food Industry Research and Develpment Institute (TW)

( * ) Notice: Subject to any disclaimer, the term of this patent is extended or adjusted under 35 U.S.C. 154(b) by 0 days.

(21) Appl. No.: 09/759,778

(22) Filed: Jan. 12, 2001

(51) Int. Cl.⁷ .................................................. C12N 1/14
(52) U.S. Cl. ............... 435/254.1; 435/156; 435/254.11; 435/911
(58) Field of Search ........................... 435/158, 254.11, 435/254.1, 911

(56) References Cited

U.S. PATENT DOCUMENTS 4,939,091 A   7/1990  Sasaki et al.
5,036,011 A   7/1991  Sasaki et al.
5,902,739 A   5/1999  Abe et al.

FOREIGN PATENT DOCUMENTS

JP        09154589        6/1997

OTHER PUBLICATIONS

Dooms et al., "Polyol synthesis and taxonomic characters in the genus", Antonie van Leeuwenhoek 37 (1971) 107–118.
Hajny et al., "Erythritol Production by a Yeastlike Fungus", Applied Microbiology, vol. 12, No. 3. p 240–246, May, 1964.
Park, Y.K., Koo, M.H., and Oliverura, I.M.A. (1996) Biochemical characteristics of osmophilic yeasts isolated form pollens and honey. Biosci. Biotech. Biochem. 60 (11): 1872–1873.
Ishizuka et al (1989) J. Ferment. Bioeng. 68:310–314.

*Primary Examiner*—Herbert J. Lilling
(74) *Attorney, Agent, or Firm*—Fish & Richardson P.C.

(57) ABSTRACT

An isolated strain of the Moniliella species that converts glucose to erythritol with a conversion rate of at least about 45% is disclosed, as is a method of producing erythritol from such a strain.

9 Claims, No Drawings

ERYTHRITOL— PRODUCING MONILIELLA STRAINS

BACKGROUND

Erythritol is a sugar alcohol that can be found in lichens, hemp leaves, and mushrooms. It is also savored in fermented foods such as wine, soya sauce, or saki (Sasaki, T. (1989) Production technology of erythritol. *Nippon Nogeikagaku Kaishi* 63: 1130–1132). Erythritol is a four-carbon polyol, which possesses several properties such as sweetness (about 70–80% of sucrose), tooth friendliness, very low calorific value (0.3 kcal/g, a tenth of sucrose), non-carcinogenicity and, unlike other polyols, causes little, if any, gastrointestinal discomfort (Harald and Bruxelles (1993) *Starch/Starke* 45:400–405).

Traditional industrial erythritol production is carried out by adding catalysts such as hydrogen and nickel to the raw material sugars under the environment of high temperature and high pressure. Another process is performed by the chemo-reduction of raw materials such as meso-tartarate (Kent, P. W., and Wood, K. R. (1964) *J. Chem. Soc.* 2493–2497) or erythrose (Otey, F. H., and Sloan, J. W. (1961) *Ind Eng. Chem.* 53:267) to obtain erythritol. In addition, erythritol can be produced by a number of microorganisms. Such organisms include high osmophilic yeasts, e.g., Pichia, Candida, Torulopsis, Trigonopsis, Moniliella, Aureobasidium, and Trichosporon sp. (Onishi, H. (1967) *Hakko Kyokaish* 25:495–506; Hajny et al. (1964) *Appl. Microbiol.* 12:240–246; Hattor, K., and Suziki, T. (1974) *Agric. Biol. Chem.* 38:1203–1208; Ishizuka, H., et al. (1989) *J. Ferment. Bioeng.* 68:310–314.)

SUMMARY

The invention features isolated strains of the Moniliella species with enhanced capacities for the conversion of glucose to erythritol. Such strains can produce erythritol from glucose with a conversion rate of at least about 35%, 40%, 45%, 50%, 55%, 60%, 65% or greater under optimal conditions.

Strains of the invention include isolates of Moniliella from a natural source; and the mutants of a Moniliella strains, e.g., a Moniliella strains assigned the American Type Culture Collection (ATCC) accession numbers of PTA-1227, PTA-1228, PTA-1229, PTA-1230, and PTA-1232. One particular mutant strain is the isolated strain, N61188-12, deposited with the American Type Culture Collection with the accession number PTA-2862.

As used herein, the term "mutant" refers to a strain whose genetic composition differs by at least one nucleotide, e.g., a substitution, insertion, or deletion, relative to a reference or parent strain. A mutant of the invention can be produced by a number of methods. One method is the selection of strains with increased erythritol conversion rates relative to a parent strain. The strains can be obtained by random mutagenesis of the parent strain, e.g., by means of a chemical mutagen, a transposon, or irradiation. In addition, a mutant strain of the invention can include a recombinant nucleic acid sequence. For example, a mutant may be a strain that harbors an additional nucleic acid sequence, e.g., a sequence transformed, transduced, or otherwise inserted into a cell of the parent strain. The additional nucleic acid sequence can encode a polypeptide that is generally or conditionally expressed. Alternatively, the additional nucleic acid sequence can encode a nucleic acid sequence capable of altering cell physiology, e.g., an anti-sense, a ribozyme, or other nucleic acid sequence. In another instance, the inserted nucleic acid is inserted into an endogenous gene, and alters (e.g., enhances or disrupts) its function. For example, the inserted nucleic acid can be a knockout construct that inactivates the endogenous gene; or an artificial enhancer or promoter that increases transcription of the endogenous gene. The mutation can disrupt the ability of the parental strain to import, assimilate, or consume erythritol or mannitol.

The invention also features a method of producing erythritol. The method includes growing a Moniliella strain of the invention, e.g., an enhanced mutant, in a culture; and purifying erythritol from the culture, e.g., from the supernatant or from the cell pellet.

The details of one or more embodiments of the invention are set forth in the accompanying drawings and the description below. Other features, objects and advantages of the invention will be apparent from the description and drawings, and from the claims.

DETAILED DESCRIPTION

The fungus Moniliella is capable of fermenting simple sugars to produce erythritol, a well-relished component of many cuisines. Screening and mutagenesis are used to identify improved strains of Moniliella that are capable of highly efficient erythritol production yields. Such strains are ideal for large-scale erythritol production, as can be achieved by the exemplary methods described herein.

Isolation of Enhanced Erythritol Producing Strains

Isolates of Moniliella can be obtained from a natural source as described in U.S. patent application Ser. No. 09/585,926, filed Jun. 2, 2000, now U.S. Pat. No. 6,300,107. For example, isolates of Moniliella can be obtained natural sources having high sugar content include honey, preserved fruit, and pollen. Each strain is identified based on its capability to convert glucose to erythritol and its various morphological and physiological traits. As used herein, the "glucose-to-erythritol conversion rate" is defined as the amount of erythritol produced divided by the amount of glucose consumed. The resulting ratio can be expressed as a percentage. The glucose-to-erythritol conversion rate of a fungal strain can be calculated by the following method. The strain is first cultured in a 10-ml broth containing 30% glucose and 1% yeast extract (initial cell density $1 \cdot 10^5$ cells/ml) in a 50 ml flask in a rotary shaker at 150 rpm and 30° C. for 6 days. Then, both the concentration of erythritol in the medium and the concentration of glucose in the medium are determined. The conversion of 1 g of glucose into 0.3 g of erythritol is termed a 30% conversion rate. The morphological traits are determined following growth on 4% malt extract, 0.5% yeast extract agar for 10 days at 20° C. See The Yeasts, A Taxonomic Study, Edited by Kurtzman et al., 4th Ed., page 785, Elsevier, Amsterdam (1998)

A mutant of a Moniliella strain can be obtained by the mutagenesis method described in Ishizuka, et al. (1989) *J. Ferment. Bioeng.* 68:310–314, or a variation thereof (see also U.S. Pat. No. 5,036,011). One variation for the mutagenesis of Moniliella cells with N-methyl-N-nitrosoguanidine (NTG) is described as follows. Moniliella cells are inoculated in broth with 30% glucose and 1% yeast extract, and cultured overnight at 30° C. on a rotary shaker at 150 rpm. This culture is diluted 1:100 into 10 ml of broth with 30% glucose, and incubated at 30° C. on a rotary shaker at 150 rpm for 1 day. The culture broth is centrifuged at 3,000 rpm for 15 min to form a cell pellet and the supernatant is discarded. The cell pellet is washed with 10 ml of sterile 0.1 M pH 7.0 phosphate buffered saline (PBS). The suspension is centrifuged (3,000 rpm, 15 min) and the supernatant is again discarded. The cells are resuspended in PBS, with 150 µg/ml NTG for 10 minutes.

After treatment with NTG, the Moniliella cells are grown in a glucose solution for 3 hours. The culture is then diluted appropriately and spread onto the medium containing 65% glucose and incubated at 30° C. for 6 days. Colonies are selected randomly, inoculated into broth containing 30% glucose, and incubated at 30° C. on a rotary shaker at 150 rpm overnight. A 1:100 dilution of the overnight culture is used to inoculate into a 30% glucose solution (10 ml) that is incubated at 30° C. on a rotary shaker at 150 rpm for 4 days. The medium from this culture is then centrifuged at 12,000 rpm for 10 min. The supernatant is diluted appropriately and the amount of residual glucose is measured using the DNS method (see below). Cultures with higher glucose consumption (i.e., lower residual glucose) are further analyzed to determine erythritol yield. The HPLC method described below can be used to quantitate erythritol yield. Cultures with indications of elevated erythritol yield are subject to further verification. For example, individual colonies are obtained for the culture, re-grown as described above, and reanalyzed. Selected colonies can be improved by additional rounds of mutagenesis according to these procedures.

Measurement of Residual Glucose 4-day-old culture broth is collected and centrifuged at 12,000 rpm for 10 min. The supernatant is diluted appropriately. 1 ml of each diluted solution is added to 0.5 ml of DNS (dinitrosalicylic acid) reagent. DNS reagents (e.g., a. 1% 3,5-dinitrosalicylic acid (DNS). b. 0.2% phenol; c. 0.05% $NaHSO_3$ or 0.025% $Na_2S_2O_3$; d. 1% NaOH; e, 0.5% potassium sodium tartrate tetrahydrate) were prepared and used according to method described in Miller, G. L. (1958) *Anal. Chem.* 31:426–428. The mixture is mixed well and incubated at 100° C. for 5 min. After cooling under room temperature, 9 ml water is added and the absorbance at 540 nm ($OD_{540\ nm}$) is determined. The absorbance at 540 nm is used to determine the concentration of glucose by comparison with the standard curve, obtained by measuring pure glucose at various concentrations.

Measurement of Erythritol Concentration

The amount of erythritol in a supernatant can be quantitated by HPLC and TLC, e.g., to determine the erythritol-producing capacity of a strain. HPLC analysis is performed by Hewlett Packard H4033A analyzer on an Ion-300 chromatography column, using 0.1 N sulfuric acid as the flowing phase with a flowing rate of 0.4 ml/min, the temperature being set at 75° C. For TLC analysis, the Neissner et al. procedure is followed. (Neissner, et al. 1980. Herstellung, aanalyse und DC-trennung von fettsaure erythritpartialestem. FETTE SEIFEN ANSTRICHMITTEL. 82:10–16.). After rinsing Kieselgel 60F254(Merck) with 4% boric acid, the gel is heated in an incubator at 105° C. for 20 minutes before use. The spreading solvent is ethylmethylketone:acetone:water (100: 10:10 by vol.) and the color-developing agent is $KMnO_4$ in concentrated sulfuric acid.

Erythritol purified from a supernatant by HPLC or TLC can be further purified by extraction and then dried under reduced pressure. The further purified product and an erythritol standard are acetylated according to the method of Shindou et al. (Shindou et al. 1989. *J. Agric. Food Chem.* 37:1474–1476.). Erythritol standards are commercially available, e.g., from Merck, Germany. The resulting sample can be assayed by GC-MS to determine if the re-purified product was identical to that of the standard sample.

Large Scale Production of Erythritol

Following the specific examples provided below, a skilled artisan can optimize erythritol yield of a mutant Moniliella strain by identifying preferred pH, temperature, and carbon source for growth and fermentation. Similar analysis can be used to optimize aeration, stirring speed, culture volume, and culture time.

To produce erythritol on a larger scale, 0.2 ml of Moniliella cells preserved in glycerol are added to 50 ml of broth in a 500 ml flask, and incubated at 30° C. on a rotary shaker at 150 rpm for about 24 hours. From this culture, 2 ml are used to inoculate a second 500 ml flask with 50 ml of broth. The second culture is incubated at 30° C. on a rotary shaker at 150 rpm for 48 hours. The second culture broth is used to inoculate 2 L of broth in a 5 L fermentor (NBS. Edison, New Jersey, USA). The culture conditions are as follows. Aeration: 1 VVM; stirred speed: 500 rpm; temperature: 30° C.; culture period: 5–7 days.

For these purposes, the broth can consist of 30%, 35%, 40%, 45%, or 50% glucose, together and 1% yeast extract. In addition, KM72 and KM72F (Shin Etsu, Shin-Etsu Chemical Co., Ltd. 6–1, Ohtemachi 2-chome, Chiyoda-ku, Tokyo, Japan) can be used as a defoamer.

Purification of Erythritol

Media from the fermentor is centrifuged to separate the culture supernatant from pelleted cells. The supernatant is decolored by passage over active carbon (e.g., powdered carbon as can be obtained from a local supplier). The decolored supernatant is desalted and de-proteinated by consecutive passage of over a cation exchange resin, DIAION, WA30 (Mitsubishi) and an anion exchange resin, AMBERLITE IR120 NA (Rohm and Haas Company). The resulting solution is concentrated with the following apparati: EYELA Rotary Vacuum Evaporator N-N Series; EYELA Waterbath SB-450; and EYELA, Aspirator A-3 (Tokyo Rikakikai Co. LTD). The concentrated solution is crystallized at room temperature. Crystals are optionally washed with or re-crystallized in hydrous alcohol and water (e.g., at 4° C.) to remove the trace impurities.

Verification of Erythritol Purification

To confirm the chemical identity of the purified product, the NMR spectra of the purified product is compared to the NMR spectra of a standard, e.g., erythritol purchased from Merck Co. (N.J, USA), or another commercial supplier. The samples are dissolved in 100% $D_2O$ and placed in an NMR spectrometer (Bruker AM-500, Germany). The following conditions are used for $^1H$ NMR spectra: 400.135 MHz; pulse length: 4.0 µs; acquisition time: 1.245 sec; pulse delay: 1 sec; chemical shifts: $D_2O$ as 0 ppm. The following conditions are used for $^{13}C$ NMR spectra: 100.536 MHz; pulse length: 5.0 µs; acquisition time: 0.623 sec; pulse delay: 2 sec; chemical shifts: 10 mM DSS as 0 ppm.

A skilled artisan can obtain a fungal mutant of the invention and utilize it to the fullest extent to produce erythritol based on the guidance of the following specific example, which is merely illustrative, and not limitative of the scope of the invention. All publications cited herein are incorporated in their entirety by reference.

EXAMPLE

Moniliella Mutant Isolation

The erythritol-producing fungi Moniliella PTA-1230 was mutagenized with NTG by the method described above. The procedure was repeated such that an improved erythritol producer isolated in one round is used as the parent strain for the subsequent round. The N61188-12 mutant strain (ATCC deposit PTA-2862) was isolated after six rounds of mutagenesis.

The N61188-12 mutant strain and the parental PTA-1230 were cultured in broth containing 35% glucose and 1% yeast extract on rotary shaker at 150 rpm for 6 days at the temperature of 25° C., 30° C., 34° C., and 37° C. At each of these temperatures, the glucose-to-erythritol conversion rates were respectively: 43.9%, 61.4%, 17.8%, and 2.2%, for the N61188-12 mutant strain; and 18.9%, 30.5%, 17.9%, and 7.7% for the parental PTA-1230. At 25° C. and 30° C., the erythritol yields of the N61188-12 strain were at least twice as great as that of the PTA-1230. The 61.4% yield observed for the N61188-12 strain was unexpected, as it is remarkably close to the theoretical upper limit for complete conversion of glucose to erythritol—68%.

For the purposes of verification, pure erythritol was obtained from a fermentor culture of the N61188-12 strain using the above-described methods. The pure erythritol from N61188-12 was analyzed by nuclear magnetic resonance as described above. Its spectra were identical to the spectra of an erythritol standard indicating that the product recovered, purified, and crystallized was, indeed, erythritol.

Optimization of Erythritol Production Conditions.

The erythritol yields were determined in parallel for the parental PTA-1230 and the N61188- 12 strain under conditions of varying pH, temperature (see above), and carbon source.

pH. The parental PTA-1230 and the N61188-12 strains were cultured in 35% glucose and 1% yeast extract broth adjusted to various pH's at 30° C. on a rotary shaker at 150 rpm for 6 days. For the pH's 3.0, 4.0, 5.0, 6.0, and 7.0, the erythritol yield of the PTA-1230 was 31.2%, 39.3%, 38.4%, 34.4%, and 34.2% respectively, whereas the erythritol yield of the N61188-12 strain was 56.6%, 59.4%, 58.5%, 60.3%, and 57.3%, respectively.

Glucose concentration. Culture broths containing 20%, 30%, 35%, 40%, and 50% glucose together with 1% yeast extract were prepared. Both PTA-1230 and N61188-12 strains were cultured in the above broths at 30° C. on a rotary shaker at 150 rpm for 6 days. At each of these glucose concentrations, the erythritol yield of the PTA-1230 strain was 40.6%, 37.1%, 34.5%, 29.4%, and 19.2%, respectively, whereas the erythritol yield of the N61188-12 strain was 56.3%, 57.5%, 62.8%, 55.6%, and 35.8%, respectively (Table 10). The optimal yield of the PTA-1230 strain was with the 20% glucose solution, the yield decreasing with the increasing glucose concentration. The optimal yield of the N61188-12 strain was with the 35% glucose broth. The yields obtained from other glucose concentrations, such as 20%, 30%, and 40% glucose solution, were similar to each other, while that obtained from 50% glucose solution was reduced to 35.8%. At high glucose concentrations, e.g., 40% and 50%, the erythritol yield of the N61188-12 strain was nearly twice that of the PTA-1230 strain. These results indicate the unexpectedly improved erythritol production capacity of the N61188-12 strain in comparison to the wild type PTA-1230 strain.

Carbon source. The culture broths containing 35% of either glucose, maltodextrin, maltose, sucrose, fructose, or lactose as carbon source, and 1% yeast extract as nitrogen source were prepared. Both PTA-1230 and N61188-12 strains were cultured in above broths at 30° C. on a rotary shaker at 150 rpm for 6 days. Respectively for glucose, maltodextrin, maltose, sucrose, fructose, or lactose, strain PTA-1230 produced 120.8, 44.5, 0, 154.0, 111.0, and 0 g/L of erythritol, whereas the N61188-12 strain produced 220.0, 15.1, 22.8, 239.4, 211.4, and 0 g/L. These results indicated that sucrose has best conversion capacity for both fungal strains, and the next being glucose, and then fructose. Notably, strain PTA-1230 cannot utilize maltose and lactose for erythritol production, whereas the N61188-12 strain can utilize maltose, but not lactose for erythritol production. For the PTA-1230 strain, the erythritol yield using sucrose as the carbon source was 27.5% higher than that using glucose, whereas the yield was only 9% higher under the same conditions for the N61188-12 strain.

Byproduct accumulation. The concentrations of the metabolic byproducts—glycerol, pentitol, and alcohol—were monitored in the aforementioned carbon sources. For example, when glucose was used as the carbon source, the concentration of glycerol and pentitol in the PTA-1230 strain culture broth was 36.4 and 17.2 g/L, respectively, whereas there was no glycerol present, and the content of pentitol was only 3.8 g/L in the N61188-12 strain culture broth. Results for additional carbon sources are illustrated in Table 1.

No alcohol was producing during the fermentation of the PTA-1230 strain with glucose as the carbon source. However, in other carbon sources, both the PTA-1230 and N61188-12 strains produced alcohol for the initial five days after inoculation. However, the alcohol was exhausted on the $6^{th}$ day. The only exception was some residual alcohol (0.7 g/L) on the $6^{th}$ day when fructose was used for the N61188-12 culture. In sum, these results indicate that the use of sucrose for culturing the N61188-12 strain results in a high conversion capacity to erythritol without the accumulation of byproducts.

TABLE 1

Production of erythritol and byproducts of PTA-1230 and N61188-12 strains

| Carbon Source | Byproducts from PTA-1230 strain (g/L) | | | | Byproducts from N61188-12 strain (g/L) | | | |
| --- | --- | --- | --- | --- | --- | --- | --- | --- |
| | Ery-thritol | Gly-cerol | Pen-titol | Alco-hol | Ery-thritol | Gly-cerol | Pen-titol | Alco-hol |
| glucose | 120.8 | 36.4 | 17.2 | 0 | 220 | 0 | 3.8 | 0 |
| malto-dextrin | 45.5 | 0 | 0 | 0 | 15.1 | 0 | 0 | 0 |
| maltose | 0 | 0 | 0 | 0 | 22.8 | 0 | 0 | 0 |
| sucrose | 154 | 23.4 | 0 | 0 | 239.4 | 0 | 0 | 0 |
| fructose | 111 | 26.3 | 7.6 | 0 | 211.4 | 13.6 | 4.2 | 0.7 |

Each carbon source was present at 35%; nitrogen source 1% yeast extract; and incubation at 150 rpm, 6 days.

Gross properties of mutant strain N61188-12. The parental PTA-1230 strain and the mutant N61188-12 strain were grown under various conditions and compared. Their cell morphologies were substantially the same. However, on plates, the mutant strain grew to only a quarter the size of the PTA-1230 strain. Notably, the two strains have different physiological properties. These differences are reflected in their abilities to ferment and assimilate different sugars. The mutant N61188-12 strain can ferment galactose (Table 2), whereas the PTA-1230 strain cannot. In addition, the N61188-12 strain is unable to assimilate erythritol and mannitol (Table 3) in contrast to the PTA-1230 strain.

TABLE 2

Fermentation of various carbon sources

| Carbon source | PTA-1230 strain | N61188-12 strain |
| --- | --- | --- |
| glucose | + | + |
| galactose | − | + |
| maltose | + | + |

TABLE 2-continued

Fermentation of various carbon sources

| Carbon source | PTA-1230 strain | N61188-12 strain |
|---|---|---|
| sucrose | + | + |
| lactose | − | − |

TABLE 3

Assimilation study of PTA-1230 and N61188-12 strains on various carbon sources

| Carbon source | PTA-1230 strain | N61188-12 strain | arbon source | PTA-1230 strain | N61188-12 strain |
|---|---|---|---|---|---|
| glucose | + | + | ribitol | − | − |
| galactose | − | − | xylitol | − | − |
| sorbose | − | − | arabinitol | − | − |
| glucosamine | − | − | glucitol | − | − |
| ribose | − | − | mannitol | + | − |
| xylose | − | − | galactitol | − | − |
| L-arabinose | − | − | myo-inositol | − | − |
| D-arabinose | − | − | glucono-1,5-lactone | + | − |
| rhamose | − | − | 2-keto-gluconate | − | − |
| sucrose | + | + | gluconate | − | − |
| maltose | + | + | glucuronate | − | − |
| trehalose | − | − | galacturona | − | − |
| methyl-D-glucoside | − | − | lactate | − | − |
| cellobiose | + | + | succinate | + | + |
| salicin | − | − | citrate | − | − |
| arbutin | + | + | methanol | + | + |
| melibiose | − | − | ethanol | − | − |
| lactose | − | − | propane | − | − |
| raffinose | − | − | butane | − | − |
| melezitose | − | − | quinate | − | − |
| inulin | − | − | saccarate | − | − |
| glycerol | + | + | galactonate | − | − |
| erythritol | + | W* | | | |

W*refers to weak growth and meager assimilation of the carbon source.

Cell density. Under various conditions such as temperature, pH, carbon source, and glucose concentration, the turbidity ($A_{660}$) of the culture broth for the N61188-12 strain was less than that of the PTA-1230 strain. Overall (except for use of maltose and lactose as the carbon source), the turbidity of the culture broth for the N61188-12 strain was between 31% and 77% of that for the PTA-1230 strain. Inmost cases the turbidity of the N61188-12 strain was less than 50% of the PTA-1230 strain. Thus, it is inferred that the N61188-12 strain reduced the proportion of carbon source applied to cell growth, and instead converted a greater proportion of the carbon source into erythritol.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. An isolated strain of the Moniliella species, wherein the strain converts glucose to erythritol with a conversion rate of at least about 45% and is a mutant of the Moniliella strain PTA-1227, PTA-1228, PTA-1229, PTA-1230, or PTA-1232.

2. The isolated strain of claim 1 wherein the strain converts glucose to erythritol with a conversion rate of at least about 50%.

3. The isolated strain of claim 2 wherein the strain converts glucose to erythritol with a conversion rate of at least about 60%.

4. The isolated strain of claim 1 wherein the strain is a mutant of the Moniliella strain PTA-1227.

5. The isolated strain of claim 1 wherein the strain is a mutant of the Moniliella strain PTA-1228.

6. The isolated strain of claim 1 wherein the strain is a mutant of the Moniliella strain PTA-1229.

7. The isolated strain of claim 1 wherein the strain is a mutant of the Moniliella strain PTA-1230.

8. The isolated strain of claim 1 wherein the strain is a mutant of the Moniliella strain PTA-1232.

9. The isolated strain of claim 7 wherein the strain is N61188-12, deposited with the Amrerican Type Culture Collection with the accession number PTA-2862.

* * * * *